United States Patent
Mandeville, III et al.

(10) Patent No.: US 6,726,905 B1
(45) Date of Patent: *Apr. 27, 2004

(54) POLY (DIALLYLAMINES)-BASED PHOSPHATE BINDERS

(75) Inventors: W. Harry Mandeville, III, Lynnfield, MA (US); Stephen Randall Holmes-Farley, Arlington, MA (US)

(73) Assignee: Genzyme Corporation, Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 902 days.

(21) Appl. No.: 08/964,498

(22) Filed: Nov. 5, 1997

(51) Int. Cl.[7] .......................... A61K 31/787; A61P 3/00

(52) U.S. Cl. ................... 424/78.35; 424/78.12; 424/78.18

(58) Field of Search .............. 424/78.1, 78.18, 424/78.19, 78.12, 78.35, 78.32

(56) References Cited

U.S. PATENT DOCUMENTS

| | | | |
|---|---|---|---|
| 2,456,428 A | 12/1948 | Parker | 260/80 |
| 2,874,132 A | 2/1959 | Riener | 260/2.1 |
| 3,288,770 A | 11/1966 | Butler | 260/88.3 |
| 3,308,020 A | 3/1967 | Wolf et al. | 167/65 |
| 3,383,281 A | 5/1968 | Wolf et al. | 167/65 |
| 3,562,266 A | 2/1971 | Minisci et al. | 260/247 |
| 3,624,209 A | 11/1971 | Granatek et al. | 424/79 |
| 3,692,895 A | 9/1972 | Nelson et al. | 424/78 |
| 3,780,171 A | 12/1973 | Irmscher et al. | 424/79 |
| 3,787,474 A | 1/1974 | Daniels et al. | 260/459 |
| 3,801,641 A | 4/1974 | Payot et al. | 260/567.6 M |
| 3,803,237 A | 4/1974 | Lednicer et al. | 260/584 R |
| 3,980,770 A | 9/1976 | Ingelman et al. | 424/79 |
| 4,027,009 A | 5/1977 | Grier et al. | 424/78 |
| 4,071,478 A | 1/1978 | Shen et al. | 260/2 R |
| 4,098,726 A | 7/1978 | Wagner et al. | 528/403 |
| 4,101,461 A | 7/1978 | Strop et al. | 521/32 |
| 4,111,859 A | 9/1978 | Strop et al. | 521/33 |
| 4,143,130 A | 3/1979 | Imondi et al. | 424/81 |
| 4,181,718 A | 1/1980 | Mason et al. | 424/180 |
| 4,205,064 A | 5/1980 | Wagner et al. | 424/78 |
| 4,217,429 A | 8/1980 | Wagner et al. | 525/411 |
| 4,247,393 A | 1/1981 | Wallace | 210/638 |
| 4,340,585 A | 7/1982 | Borzatta et al. | 424/79 |
| 4,426,489 A | 1/1984 | Wessling et al. | 524/815 |
| 4,504,640 A | 3/1985 | Harada et al. | 526/193 |
| 4,540,760 A | 9/1985 | Harada et al. | 526/211 |
| 4,557,930 A | 12/1985 | Kihara et al. | 424/79 |
| 4,559,391 A | 12/1985 | Ueda et al. | 525/366 |
| 4,605,701 A | 8/1986 | Harada et al. | 525/107 |
| 4,680,360 A | 7/1987 | Ueda et al. | 526/310 |
| 4,759,923 A | 7/1988 | Buntin et al. | 424/440 |
| 5,055,197 A | 10/1991 | Albright et al. | 210/638 |
| 5,189,111 A | 2/1993 | Danner | 525/328.2 |
| 5,236,701 A | 8/1993 | St. Pierre et al. | 424/78.12 |
| 5,302,531 A | 4/1994 | Bauer | 436/74 |
| 5,374,422 A | 12/1994 | St. Pierre et al. | 424/78.12 |
| 5,414,068 A | 5/1995 | Bliem et al. | 528/288 |
| 5,428,112 A | 6/1995 | Ahlers et al. | 525/326.7 |
| 5,430,110 A | 7/1995 | Ahlers et al. | 525/328.2 |
| 5,451,397 A | 9/1995 | Albright et al. | 424/78.01 |
| 5,462,730 A | 10/1995 | McTaggart et al. | 424/78.35 |

FOREIGN PATENT DOCUMENTS

| | | |
|---|---|---|
| EP | 0 081 291 | 6/1983 |
| EP | 0 162 388 | 11/1985 |
| EP | 0 373 852 | 6/1990 |
| EP | 0 375 350 | 6/1990 |
| EP | 0 432 995 | 6/1991 |
| EP | 0 459 632 | 12/1991 |
| EP | 0 605 757 | 7/1994 |
| EP | 0 793 960 A1 | 10/1997 |
| GB | 798488 | 7/1958 |
| GB | 929391 | 6/1963 |
| GB | 1 567 294 | 5/1980 |
| GB | 1 573 487 | 8/1980 |
| GB | 2 090 605 | 7/1982 |
| GB | 2 276 170 | 9/1994 |
| WO | 91/18027 | 11/1991 |
| WO | 92/10522 | 6/1992 |
| WO | 94/04596 | 3/1994 |
| WO | 94/19379 | 9/1994 |
| WO | 94/27620 | 12/1994 |
| WO | 95/05184 | 2/1995 |
| WO | 95/34585 | 12/1995 |
| WO | 95/34588 | 12/1995 |
| WO | 96/21454 | 7/1996 |
| WO | 96/25440 | 8/1996 |
| WO | WO 96/39156 | 12/1996 |

OTHER PUBLICATIONS

Physicians' Desk Reference, Consult 1992 Supplements for Revisions "Phoslo®", Calcium Acetate Tablets.

Physicians' Desk Reference, Consult 1992 Supplements for Revisions "Amphojel®", Suspension Tablets.

Burt, H.M., et al., "Ion–Exchange Resins as Potential Phosphate–Binding Agents for Renal Failure Patients: Effect of the Physicochemical Properties of Resins on Phosphate and Bile Salt Binding," *J. of Pharmaceutical Sciences*, 76(5):379–383 (1987).

(List continued on next page.)

*Primary Examiner*—Edward J. Webman
(74) *Attorney, Agent, or Firm*—Hamilton, Brook, Smith & Reynolds, P.C.

(57) ABSTRACT

The present invention relates to a method for lowering the serum phosphate level of a patient. The method comprises the step of administering to the patient a therapeutically effective amount of a polymer characterized by a diallylamine monomer or repeat unit. The amino nitrogen atom of the diallylamine repeat unit can be substituted by one or two substituents independently selected from among substituted and unsubstituted, normal, branched and cyclic alkyl groups, and aryl groups. When the diallylamine repeat unit comprises an ammonium or quaternary ammonium group, the monomer will further comprise a suitable anion, such as a conjugate base of a pharmaceutically acceptable acid.

28 Claims, No Drawings

OTHER PUBLICATIONS

Delmez, J.A., et al., "Hyperphosphatemia: Its Consequences and Treatment in Patients with Chronic Renal Disease," *American Journal of Kidney Diseases*, XIX (4):303–317 (1992).

Emmett, M., et al., "Calcium Acetate Control of Serum Phosphorus in Hemodialysis Patients," *American Journal of Kidney Diseases*, XVII(5) :544–550 (1991).

Ghosh, J.P., et al., "Preparation and Properties of a New Chelating Resin Containing 2–Nitroso–1–Naphthol," *Talanta*, 28:957–959 (1981).

Mai, M.L., et al., "Calcium acetate, an effective phosphorus binder in patients with renal failure," *Kidney International*, 36:690–695 (1989).

Munson, Paul L., "Studies on the Role of the Parathyroids in Calcium and Phosphorus Metabolism," *Annals New York Academy of Sciences*, pp. 776–795 (Jun. 1993).

Slatopolsky, E., et al., "Calcium Carbonate as a Phosphate Binder in Patients with Chronic Renal Failure Undergoing Dialysis," *The New England Journal of Medicine*, 315(3):157–161 (1986).

Warshawsky, A., in Ion Exchange and Sorption Processes in *Hydrometallurgy Critical Reports on Applied Chemistry*, vol. 15, Chapter 4: Chelating ion exchangers, pp. 166–225 M. Streat & D. Naden (Eds.), John Wiley & Sons (1987).

Salusky, I.B., et al., "Aluminum Accumulation During Treatment with Aluminum Hydroxide and Dialysis in Children and Young Adults with Chronic Renal Disease," *The New England Journal of Medicine*, 324(8) :527–531 (1991).

Winston, A. and Kirchner, D., "Hydroxamic Acid Polymers. Effect of Structure on the Selective Chelation of Iron in Water," *Macromolecules*, 11(3) :597–603 (1978).

Winston, A. and McLaughlin, G.R., "Hydroxamic Acid Polymers. II. Design of a Polymeric Chelating Agent for Iron," *J. of Polymer Science*, 14:2155–2165 (1976).

McGary, T.J., et al., "Polycation as an Alternative Osmotic Agent and Phosphate Binder in Peritoneal Dialysis," *Uremia Investigation*, 8(2) :79–84 (1984–1985).

Butler, G.B. and Do, C.H., "Comblike Cyclopolymers of Alkyldiallylamines and Alkyldiallylmethylammonium Chlorides," in *Water–Soluble Polymers*, eds. Shalaby, McCormick & Butler, Chapter 9, pp. 151–158 ACS Symposium Series 467 (1991).

Wang, G.–J. and Engberts, J., "Study of the Conformational State of Non–Cross–Linked and Cross–Linked Poly (alkylmethyldiallylammonium Chlorides) in Aqueous Solution by Fluorescence Probing," *Gazzetta Chimica Italiana*, 125:393–397 (1995).

Wang, G.–J. and Engberts, J., "Fluorescence probing of the formation of hydrophobic microdomains by cross–linked poly(alkylmethyldiallylammonium bromides) in aqueous solution," *Recl. Trav. Chim. Pays–Bas* 113:390–393 (1994).

Harada, S. and Arai, K., "The Cyclo–copolymerization of Diallyl Compounds and Sulfur Dioxide," *Die Makromolekulare Chemie 107*:64–93 (1967).

Wang, G.–J. and Engberts, J., "Induction of Aggregate Formation of Cationic Polysoaps and Surfactants by Low Concentrations of Additives in Aqueous Solution," *Langmuir*, 10(8) :2583–2587 (1994).

Wang, G.–J. and Engberts, J., "Synthesis of Hydrophobically and Electrostatically Modified Polyacrylamides and Their Catalytic Effects on the Unimolecular Decarboxylation of 6–Nitrobenzisoxazole–3–carboxylate Anion," *Langmuir*, 11(10) :3856–3861 (1995).

Wang, G.–J. and Engberts, J., "Synthesis and Catalytic Properties of Non–Cross–Linked and Cross–Linked Poly(alkylmethyldiallylammonium bromides) Having Decyl, Octyl, and Hexyl Side Chains," *J. Org. Chem*, 60:4030–4038 (1995).

Wang, G.–J. and Engberts, J., "Synthesis and Catalytic Properties of Cross–Linked Hydrophobically Associating Poly(alkylmethyldiallylammonium bromides)," *J. Org. Chem.*, 59(15) :4076–4081 (1994).

Yang, Y. J. and Engberts, J., "Synthesis and Catalytic Properties of Hydrophobically Modified Poly(alkylmethyldiallylammonium bromides)," *J. Org. Chem.*, 56:4300–4304 (1991).

Negi, Y., et al., "Cyclopolymerization of Diallylamine Derivatives in Dimethyl Sulfoxide," *J. of Polymer Science: Part A–1*, 5:1951–1965 (1967).

Yeh, F., et al., "Nanoscale Supramolecular Structures in the Gels of Poly(Diallyldimethylammonium Chloride) Interacting with Sodium Dodecyl Sulfate," *J. Am. Chem. Soc.*, 118(28) :6615–6618 (1996).

Boothe, J.E., et al., "Some Homo– and Copolymerization Studies of Dimethyldiallylammonium Chloride," *J. Macromol. Sci.–Chem.*, A4(6) :1419–1430 (1970).

Tsuchida, E., et al., "Molecular Assembly of Cholesterol–Bearing Poly(allylamine) for Binding Bile Salts in Water," *Macromolecules*, 20:4235–4237 (1997).

Heming, A.E. and Flanagan, T.L., "Considerations in the Selection of Cation Exchange Resins for Therapeutic Use," *Annals of the New York Academy of Sciences*, 57:239–251 (1954).

McCarthy, Peter A., "New Approaches to Atherosclerosis: An Overview," *Medicinal Research Reviews*, 13(2):139–159 (1993).

Dubin, P.L. and Davis, D.D., "Quasi–Elastic Light Scattering of Polyelectrolyte–Micelle Complexes," *Macromolecules* 17:1294–1296 (1984).

Kunitake, T., et al., "Catalyses of Polymer Complexes. 4. Polysoap–Catalyzed Decarboxylation of 6–Nitrobenzisoxazole–3–carboxylate Anion. Importance of the Hydrophobic Environment in Activation of the Anion," *J. Org. Chem* 42(2):306–312 (1977).

Kuron, G.W., et al., "The Bile Acid Binding and Hypocholesterolemic Action of Two Water–Soluble Polymers," *Atherosclerosis*, 37:353–360 (1980).

Kevelam, J., et al., "Polymer–Surfactant Interactions Studied by Titration Microcalorimetry: Influence of Polymer Hydrophobicity, Electrostatic Forces, and Surfactant Aggregational State," *Langmuir*, 12(20):4709–4717 (1996).

Hodgkin, H., et al., "Use of $^{13}$C–NMR in the Study of Reactions on Crosslinked Resins," Published by John Wiley & Sons, *J. of Polymer Science: Polymer Chemistry Edition*, 19(5):1239–1249 (1981).

POLY (DIALLYLAMINES)-BASED PHOSPHATE BINDERS

BACKGROUND OF THE INVENTION

Hyperphosphatemia frequently accompanies diseases associated with inadequate renal function, hypoparathyroidism, and certain other medical conditions. Hyperphosphatemia is typically defined as a serum phosphate level of greater than about 6 mg/dL. The condition, especially if present over extended periods of time, leads to severe abnormalities in calcium and phosphorus metabolism and can be manifested by aberrant calcification in joints, lungs, and eyes.

Therapeutic efforts to reduce serum phosphate levels include dialysis, reduction in dietary phosphate, and oral administration of insoluble phosphate binders to reduce gastrointestinal adsorption. Dialysis and reduced dietary phosphate are generally unable to adequately reverse hyperphosphatemia. Further disadvantages of these therapeutic regimens include the invasive nature of dialysis and difficulties associated with modifying dietary habits.

Therapy based upon oral administration of certain phosphate binders has also been suggested. Phosphate binders include calcium or aluminum salts. Calcium salts have been widely used to bind intestinal phosphate and prevent adsorption. The ingested calcium combines with phosphate to form insoluble calcium phosphate salts, such as $Ca_3(PO_4)_2$, $CaHPO_4$, or $Ca(H_2PO_4)_2$. A variety of calcium salts, including calcium carbonate, calcium acetate (such as PhosLo® calcium acetate tablets), calcium citrate, calcium alginate and calcium ketoacid salts have been utilized for in vivo phosphate binding. The use of calcium salts, however, can result in hypercalcemia due to absorption of high amounts of ingested calcium. Hypercalcemia has been implicated in many serious side effects, such as cardiad arrhythmias, renal failure, and skin and visceral calcification. Frequent monitoring of serum calcium levels is required during therapy with calcium-based phosphate binders.

Aluminum-based phosphate binders, such as Amphojel® aluminum hydroxide gel, have also been used for treating hyperphosphatemia. These compounds complex with intestinal phosphate to form highly insoluble aluminum phosphate; the bound phosphate is unavailable for absorption by the patient. Prolonged use of aluminum gels leads to accumulations of aluminum, and often to aluminum toxicity, accompanied by such symptoms as encephalopathy, osteomalacia, and myopathy.

Selected ion exchange resins have also been suggested for use in binding phosphate. Those tested include Dowex® anion-exchange resins in the chloride form, such as XF 43311, XY 40013, XF 43254, XY 40011, and XY 40012 (Burt et al., *J. Pharmaceutical Sci.* 76: 379–383 (1987)). These. resins have several drawbacks for treatment of hyperphosphatemia, including poor binding efficiency, necessitating high doses for significant reduction of absorbed phosphate.

Thus, a need exists for improved phosphate binders which can be administered orally in acceptable dosage levels without resulting in many of the serious side effects discussed above.

SUMMARY OF THE INVENTION

The present invention relates to a method for lowering the serum phosphate level of a patient. The method comprises the step of administering to the patient a therapeutically effective amount of a polymer characterized by a diallylamine monomer or repeat unit. The amino nitrogen atom of the diallylamine repeat unit can be substituted by one or two substituents independently selected from among substituted and unsubstituted, normal, branched and cyclic alkyl groups, and aryl groups. When the diallylamine repeat unit comprises an ammonium or quaternary ammonium group, the monomer will be associated with a suitable anion, such as a conjugate base of a pharmaceutically acceptable acid.

The polymer to be administered can be a homopolymer or a copolymer. When the polymer is a copolymer, the polymer can comprise a diallyamine monomer and at least one additional monomer. The additional monomer can be a second diallylamine monomer or a monomer which is not a diallylamine, such as substituted or unsubstituted acrylamide or sulfur dioxide.

The polymer can be linear, branched or crosslinked. In one embodiment, the polymer is crosslinked via the incorporation of a multifunctional comonomer. In another embodiment, the polymer is crosslinked via bridging groups which link amino nitrogen atoms on different polymer strands.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principal features of the invention can be employed in various embodiments without departing from the,scope of the present invention.

The present invention relates to Applicant's discovery that poly(diallylamine) polymers exhibit excellent phosphate-binding activity. The invention provides a method for lowering the serum phosphate level of a patient comprising administering to the patient a therapeutically effective amount of a polymer characterized by a diallylamine or N-substituted diallylamine monomer, or repeat unit.

As used herein, the term "therapeutically effective amount" refers to an amount which is sufficient to decrease the serum phosphate level of the patient by a clinically significant amount. The patient can be an animal, for example, a mammal, or a human.

In one embodiment, the polymer to be administered is a poly(diallylamine) polymer. The polymer can be a homopolymer, wherein each of the diallylamine repeat units has the same nitrogen substituents, or a copolymer, for example, comprising two or more diallylamine repeat units having different amino nitrogen substituents. The polymer to be administered can also be a copolymer comprising one or more diallylamine repeat units and at least one additional repeat unit which is not a diallylamine. In these polymers, the diallylamine nitrogen atom can be unsubstituted or substituted with one or two substituents selected from among substituted and unsubstituted normal, branched and cyclic alkyl groups and substituted and unsubstituted aryl groups.

In one embodiment, the polymer to be administered is characterized by an amine-bearing monomeric unit of Formula

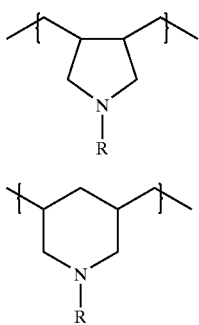

(I)

(II)

or a combination thereof, wherein R is a hydrogen atom; a substituted or unsubstituted, linear, branched or cyclic alkyl group; or a substituted or unsubstituted aryl group. Suitable alkyl and aryl substituents include halogen atoms, such as fluorine, chlorine, bromine and iodine atoms; alkyl; hydroxy; primary, secondary and tertiary amino; quaternary ammonium; alkoxy; carboxamido; sulfonamido; aryl; hydrazido; guanadyl; and ureyl. In a preferred embodiment, R is a methyl group.

In another embodiment, the polymer to be administered is characterized by a repeat unit of Formula III or of Formula IV,

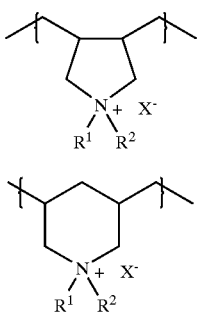

(III)

(IV)

or a combination thereof, wherein $R^1$ and $R^2$ are each, independently, hydrogen; substituted or unsubstituted linear, branched or cyclic alkyl; or substituted or unsubstituted aryl. Suitable alkyl and aryl substituents include halogen atoms, such as fluorine, chlorine, bromine and iodine atoms; hydroxy; primary, secondary and tertiary amino; quaternary ammonium; alkoxy; carboxamido; sulfonamido; aryl; hydrazido; guanadyl; and ureyl. In a preferred embodiment, $R^2$ is methyl.

In another embodiment, the polymer to be administered is characterized by a repeat unit of Formula III or Formula IV wherein $R^1$, $R^2$ and the nitrogen atom together form a cyclic structure, such as a saturated or unsaturated ring system. For example, $R^1$ and $R^2$ can together form a substituted or unsubstituted $C_1$–$C_{12}$-alkylene group, such as —$(CH_2)_n$— wherein n is from 2 to 12.

In Formulas III and IV, $X^-$ is an anion, such as the conjugate base of a pharmaceutically acceptable acid. Such anions include chloride, citrate, tartrate, lactate, methanesulfonate, acetate, formate, maleate, fumarate, malate, succinate, malonate, sulfate, hydrosulfate, L-glutamate, L-aspartate, pyruvate, mucate, benzoate, glucuronate, oxalate, ascorbate and acetylglycinate. In a preferred embodiment, $X^-$ is chloride.

In one embodiment, the polymer to be administered is characterized by a diallylamine repeat unit is of Formula I, Formula II, Formula III, or Formula IV, wherein the amino nitrogen atom is substituted with an ammonioalkyl substituent. Suitable ammonioalkyl substituents are of the general formula

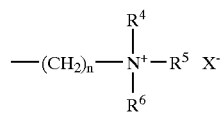

wherein $R^4$, $R^5$ and $R^6$ are each, independently, a hydrogen atom or a $C_1$–$C_{24}$ alkyl group; n is an integer from 2 to about 20, preferably from 3 to about 6; and $X^-$ is an anion, such as a conjugate base of a pharmaceutically acceptable acid. Suitable examples of ammonioalkyl groups include, but are not limited to,
4-(dioctylmethylammonio)butyl;
3-(dodecyldimethylammonio)propyl;
3-(octyldimethylammonio)propyl;
3-(dodecyldimethylammonio)propyl;
5-(dodecyldimethylammonio)pentyl;
3-cylohexyldimetahylammonio)propyl;
3-(decyldimethylammonio)-2-hydroxypropyl;
3-(tridecylammonio)propyl;
3-(docosyldimethylammonio)propyl;
4-(dodecyldimethylammonio)butyl;
3-(octadecyldimethylammonio)propyl;
3-(hexyldimethylammonio)propyl;
3-(methyldioctylammonio)propyl;
3-(didecylmethylammonio)propyl;
3-(heptyrldimethylammonio)propyl;
3-(dimethylnonylammonio)propyl;
6-(dimethylundecylammonio)hexyl;
4-(heptyldimethylammonio)butyl;
3-(dimethylundecylammonio)propyl; and
3-(tetradecyldimethylammonio)propyl.

The polymer to be administered can be a copolymer comprising a diallylamine repeat unit, such as a repeat unit of Formula I, II, III, or IV, and at least one additional monomer. In one embodiment, the polymer is a copolymer comprising at least one monomer which is not a diallylamine. Suitable examples of such monomers include substituted and unsubstituted acrylate, acrylamide, methacrylate, methacrylamide, allylamine, triallylamine, tetrallylammonium ion, allyl alcohol, vinyl amine, vinyl alcohol, sulfur dioxide, and carbon dioxide. For example, the additional monomer can be a hydrophilic monomer, such as N-(2-hydroxyethyl)acrylamide or (3-hydroxypropyl) acrylate. Also included are the multifunctional crosslinking co-monomers which are discussed in detail below. Copolymers comprising a repeat unit which is not a diallylamine can have a wide range of compositions. Typically, the diallylamine monomer will constitute from about 10% to about 90% of the repeat units within the polymer.

The polymers of use in the present method can be linear or crosslinked. The polymer can be crosslinked, for example, by the incorporation within the polymer of a multifunctional comonomer. Suitable multifunctional co-monomers include diacrylates, triacrylates and. tetraacrylates, dimethacrylates, diacrylamides, diallylacrylamide, di(methacrylamides), triallylamine and tetraalylammonium ion. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide) ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene. The amount of crosslinking agent is typically between about 1.0% and about 30% by weight relative to the weight of the polymer, preferably from about 5% to about 25% by weight.

The polymer can also be crosslinked by bridging units which link amino groups on adjacent polymer strands. Suitable bridging units include straight chain or branched, substituted or unsubstituted alkylene groups, diacylalkylene groups, diacylarene groups and alkylene bis(carbamoyl) groups. Examples of suitable bridging units include —$(CH_2)_n$—, wherein n is an integer from about 2 to about 20; —$CH_2$—$CH(OH)$—$CH_2$—; —$C(O)CH_2CH_2C(O)$—; —$CH_2$—$CH(OH)$—O—$(CH_2)_m$—O—$CH(OH)$—$CH_2$—, wherein m is an integer from about 2 to about 4; —$C(O)$—$(C_6H_2(COOH)_2)$—$C(O)$— and —$C(O)NH(CH_2)_pNHC(O)$—, wherein p is an integer from about 2 to about 20.

Advantageously, crosslinking the polymers renders the polymers non-adsorbable and stable in the patient. A "stable" polymer composition, when administered in therapeutically effective amounts, does not dissolve or otherwise decompose to form potentially harmful byproducts, and remains substantially intact.

Polymers of use in the present method are, preferably, of a molecular weight which enables them to reach and remain in the gastrointestinal tract for a sufficient period of time to bind a significant amount of phosphate. The polymers should, thus, be of sufficiently high molecular weight to resist, partially or completely, absorption from the gastrointestinal tract into other regions of the body. The resulting polymer/phosphate complex should then be excreted from the body. Suitable linear or branched (non-crosslinked) polymers have molecular weights which range from about 2,000 Daltons to about 500,000 Daltons, preferably from about 5,000 Daltons to about 150,000 Daltons. Crosslinked polymers, however, are not generally characterized by molecular weight. The crosslinked polymers discussed herein should be sufficiently crosslinked to-resist adsorption from the gastrointestinal tract.

The polymer network can be administered orally to a patient in a dosage of about 1 mg/kg/day to about 10 g/kg/day; the particular dosage will depend on the individual patient (e.g., the patient's weight and the extent of phosphate removal required). The polymer can be administered either in hydrated or dehydrated form, and can be flavored or added to a food or drink, if desired, to enhance patient acceptance. Additional ingredients such as other phosphate binders (including other polymers, calcium salts, and aluminum salts) or inert ingredients, such as artificial coloring agents, may be added as well.

Examples of suitable forms for administration include pills, tablets, capsules, and powders (i.e. for sprinkling on food). The pill, tablet, capsule or powder can be coated with a substance capable of protecting the composition from the gastric acid in the patient's stomach for a period of time sufficient for the composition to pass undisintegrated into the patient's small intestine. The polymer can be administered alone, admixed with a carrier, diluted by a carrier, or enclosed within a carrier which may be in the form of a capsule, sachet, paper or other container. When the carrier serves as a diluent, it may be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carriers, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates and talc.

The polymeric phosphate binder can be co-administered to the patient with a calcium supplement. The calcium supplement is, preferably, administered orally in an amount which is effective to increase the physiological calcium concentration of the patient. The calcium supplement can be administered prior to, simultaneous with, or subsequent to administration of the polymeric phosphate binder. The calcium supplement can be any pharmaceutically acceptable calcium salt, such as calcium acetate, calcium carbonate, calcium gluconate, calcium lactate, calcium levinulate, calcium citrate, calcium lactobionate and calcium chloride. Preferably, the calcium supplement to be administered serves as both a calcium source and a buffering agent, such as calcium carbonate or calcium acetate.

The polymeric phosphate binder and the calcium supplement can be administered individually or as components of a single composition. For example, the calcium supplement can be included in one of the polymeric phosphate binder formulations discussed above. In this case, the calcium supplement can additionally serve as a carrier or diluent for the polymeric phosphate binder. For example, the calcium supplement, such as calcium carbonate, can serve as a hardening agent in a tablet form of the polymeric phosphate binder composition. Such a composition provides the polymeric phosphate binder, a calcium supplement and a carbonate supplement in a single dosage form.

Polymers of use in the present method can be prepared using techniques known in the art of polymer synthesis (see for example, Shalaby et al., ed., *Water-Soluble Polymers*, American Chemical Society, Washington D.C. (1991)). For example, the appropriate monomer can be polymerized by methods known in the art, for example, via a free radical addition process. In this case the polymerization mixture includes a free-radical initiator, such as a free radical initiator selected from among those which are well known in the art of polymer chemistry. Suitable free-radical initiators include azobis(isobutyronitrile), azobis(4-cyanovaleric acid), azobis(amidinopropane) dihydrochloride, potassium persulfate, ammonium persulfate and potassium hydrogen persulfate. The free radical initiator is preferably present in the reaction mixture in an amount ranging from about 0.1 mole percent to about 5 mole percent relative to the monomer.

The polymer can be crosslinked, for example, by including a multifunctional co-monomer as the crosslinking agent in the reaction mixture. A multifunctional co-monomer can be incorporated into two or more growing polymer chains, thereby crosslinking the chains. Suitable multifunctional co-monomers include those discussed above. The amount of crbsslinking agent added to the reaction mixture is, generally, between 1.0% and 3b% by weight relative to the combined weight of the polymer and the crosslinking agent, and preferably from about 2.5% to about 25% by weight.

The multifunctional co-monomer can also take the form of a multifunctional diallylamine, such as a bis (diallylamino)alkane or a bis(diallylalkylammonio)alkane. Suitable monomers of this type include 1,10-bis (diallylmethylammonio)decane dibromide and 1,6-bis (diallylmethylammonio)hexane dibromide, each of which can be formed by the reaction of diallylmethylamine with the appropriate dibromoalkane.

The polymers to be administered can also be crosslinked subsequent to polymerization by reacting the polymer with one or more crosslinking agents having two or more functional groups, such as electrophilic groups, which react with amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among epoxide, acyl-X and alkyl-X, wherein X- is a suitable leaving group, such as a halide, acylate, tosylate or mesylate group. Examples of such compounds include epichlorohydrin, succinyl dichloride, butanedioldiglycidyl ether, ethanedioldiglycidyl ether, pyromellitic dianhydride and dihaloalkanes. The crosslinking agent can also be an α,ω-alkylene diisocyanate, for example $OCN(CH_2)_pNCO$, wherein p is an integer from about 2 to about 20. The polymer can be reacted with an amount of crosslinking agent equal to from about 0.5 to 40 mole percent relative to the amino groups within the polymer, depending upon the extent of crosslinking desired.

A polymer comprising alkylated amino groups can be formed by reacting a preformed polymer with a suitable alkylating agent, or by polymerizing an alkylated monomer. Suitable alkylated monomers can be prepared by reacting diallylamine or a diallylamine derivative, such as diallylmethylamine, with an alkylating agent. As used herein, the term "alkylating agent" refers to a compound which reacts with an amino group to form a nitrogen-carbon bond thereby adding an alkyl or alkyl derivative substituent to the nitrogen atom. Suitable alkylating agents are compounds comprising an alkyl group or alkyl derivative which is bonded to a leaving group, such as a halo, tosylate, mesylate or epoxy group. Examples of preferred alkylating agents include $C_1$–$C_{24}$-alkyl halides, for example, n-butyl halides, n-hexyl halides, n-decyl halides, and n-octadecyl halides; $C_2$–$C_{24}$-dihaloalkanes, for example, 1,10-dihalodecanes; $C_1$–$C_{24}$-hydroxyalkyl halides, for example, 11-halo-1-undecanols; $C_1$–$C_{24}$-arylalkyl halides, for example, benzyl halide; $C_2$–$C_{24}$-alkylepoxy ammonium salts, for example, glycidylpropyl-trimethylammonium salts; and $C_2$–$C_{24}$-epoxyalkylamides, for example, N-(2,3-epoxypropyl)butyramide or N-(2,3-epoxypropyl)hexanamide. Preferred alkylating agents include halodecane, and halododecane, where in each case "halo" represents a chloro, bromo or iodo substituent.

Diallylamine polymers-having amino groups which bear quaternary ammonium-substituted alkyl groups can be prepared using alkylating agents such as (X-alkyl)ammonium salts, wherein X represents a suitable leaving group, as described above. These compounds can be prepared by the reaction of an appropriate dihaloalkane, such as a bromochloroalkane, with a tertiary amine. Suitable alkylating agents of this type include the following:
(4-bromobutyl)dioctylmethylammonium bromide;
(3-bromopropyl)dodecyldimethylammonium bromide;
(3-chloropropyl)dodecyldimethylammonium bromide);
(3-bromopropyl)octyldimethylammonium bromide;
(3-chloropropyl)octyldimethylammonium bromide;
(3-iodobutyl)dioctylmethylammonium bromide;
(2,3-epoxypropyl)decyldimethylammonium bromide;
(3-chloropropyl)decyldimethylammonium bromide;
(5-tosylpentyl)dodecyldimethylammonium bromide;
(6-bromohexyl)octyldimethylammonium bromide;
(12-bromododecyl)decyldimethylammonium bromide;.
(3-bromopropyl)tridecylammonium bromide;
(3-bromopropyl)docosyldimethylammonium bromide;
(6-bromohexyl)docbsyldimethylammbnium bromide;
(4-chlorobutyl)dodecyldimethylammonium bromide;
(3-chloropropyl)octadecyldimethylammonium bromide;
(3-chloropropyl)hexyldimethylammonium bromide;
(3-chloropropyl)methyldioctylammonium bromide;
(3-chloropropyl)methyldidecylammonium bromide;
(3-chloropropyl)cyclohexyldimethylammonium bromide;
(3-bromopropyl)heptyldimethylammonium bromide;
(3-bromopropyl)dimethylnonylammonium bromide;
(6-bromohexyl)dimethylundecylammonium bromide;
(4-chlorobutyl)heptyldimethylammonium bromide;
(3-chloropropyl)dimethylundecylammonium bromide; and
(3-chloropropyl)tetradecyldimethylammonium bromide.

Each of the alkylating agents described above can also exist and be used as a salt in combination with an anion other than bromide. For example, these and similar alkylating agents can be prepared and used as salts with a wide range of anions, including chloride, iodide, acetate, p-toluenesulfonate and methanesulfonate.

The invention will now be further and specifically described by the following examples.

EXAMPLES

Example 1

Synthesis of Diallylmethyldodecylammonium Bromide

To a 2 L Morton flask was added diallylmethylamine (100 g), 1-bromododecane (249 g), and tetrahydrofuran (750 mL). The mixture was heated to 65° C. for 44 h, and then allowed to cool to room temperature. The solvent was removed by rotary vacuum evaporation to leave two layers. Diethylether (500 mL) was added and the mixture was stirred for 1 hr. The mixture was allowed to settle and the top layer was decanted and discarded. Additional diethylether (500 mL) was added. The mixture was stirred for 24 h, and the top layer was again decanted and discarded. The remaining oil was dried in a vacuum oven at 65° C. for 4 days to yield 67 g of product.

Example 2

Synthesis of 1,10-bis(Diallylmethylammonio) decane Dibromide

To a 1 L Morton flask was added diallylmethylamine (86.1 g), 1,10-dibromodecane (112 g), and methanol (100 mL). The mixture was heated to 65° C. for 24 h, and then allowed to cool to room temperature. The solvent was removed by rotary vacuum evaporation. Diethylether (400 mL) was added and the mixture was stirred for 1 hr. The mixture was allowed to settle and the top layer was decanted and discarded. The remaining oil was dried by rotary vacuum evaporation to yield 215 g of product.

Example 3

Synthesis of 1,6-bis(Diallylmethylammonio)hexane Dibromide

To a 1 L Morton flask was added diallylmethylamine (74.6 g), 1,6-dibromohexane (77 g), and methanol (10 mL). The mixture was heated to 65° C. for 17 h, and then allowed to cool to room temperature. Diethylether (300 mL) was added and the mixture was stirred for 1 hr. The solid was collected by filtration and resuspended in diethylether (200 mL). The mixture was stirred for 1 hr, and the solid again collected by filtration. The solid was then dried in a vacuum oven at 50° C. for 3 days to yield 136 g of product.

Example 4

Synthesis of Poly[1,10-bis(Diallylmethylammonio) decane Dibromide]

To a 250-mL round bottom flask was added 1,10-bis (diallylmethylammonio)decane dibromide (20 g) and water (40 g). 2,2'-Azobis(2-amidopropane, dihydrochloride (0.5 mL of a 50% aqueous solution) was added and nitrogen was bubbled through the mixture for 1 hr. The mixture was then heated to 60° C. with stirring for 4 hr, at which time additional 2,2'-Azobis(2-amidopropane, dihydrochloride (0.5 mL of a 50% aqueous solution) was added.

After 18 h the solution was allowed to cool to room temperature. The resulting gel was removed and ground in a blender with water (500 mL). The solid was collected by centrifugation and resuspended in methanol (500 mL). After stirring for 1 hr, the solid was collected by filtration and resuspended in aqueous NaCl (500 mL of 1.5 M solution). After again stirring for 1 hr, the solid was collected by filtration. The aqueous NaCl rinse was repeated twice more, and the solid was rinsed with water until the conductivity of the rinse reached 0.3 mS/cm. The solid was dried in a forced air at 60° C. to yield 10.0 g of product.

Example 5

Synthesis of Copoly[1,10-bis (diallylmethylammonio)decane Dibromide/ Diallylmethyldodecylammonium Bromide]

To a 500-mL round bottom flask was added 1,10-bis (diallylmethylammonio)decane dibromide (21.1 g), diallyl-methyldodecylammonium bromide (21.1 g), and water (52 g). 2,2'-Azobis(2-amidmopropane) dihydrochloride (1 mL of a 50% aqueous solution) was added and nitrogen was bubbled through the mixture for 1 hr. The mixture was then heated to 60° C. with stirring for 18 hr. The resulting gel was allowed to cool to room temperature. The gel was removed and ground in a blender with water (250 mL). The solid was collected by filtration and resuspended in methanol (250 mL). The solid was collected by filtration and resuspended in methanol (250 mL). After stirring for 1 hr, the solid was collected by filtration and resuspended in aqueous NaCl (250 mL of 1.5 M solution). After again stirring for 1 hr, the solid was collected by filtration. The aqueous NaCl rinse was repeated twice more, and the solid was rinsed with water until the conductivity of the rinse reached 0.08 mS/cm. The solid was dried in a forced-air oven at 60° C. to yield 17.6 g of product.

Example 6

Synthesis of Epichlorohydrin Crosslinked Poly (diallylmethylamine)

A crosslinked gel of N-methyl-N,N-diallylamine polymer was prepared by reacting the corresponding linear soluble polymer with epichlorohydrin. The starting material, poly (diallylmethylamine) was obtained in the form of its hydrochloride salt from Nitto Boseki Co. The polymer was obtained as a 60% aqueous solution.

The polymer solution (83g) was diluted with 170 mL of deionized water. While stirring, 6.8 g of NaOH was added to the polymer solution. The reaction mixture was allowed to stir until all NaOH had dissolved. When the temperature of the solution had dropped below 30° C., epichlorohydrin (1.2 mL) was added and stirring continued. The reaction medium slowly became viscous and after about 80 minutes, had gelled and the stirring was stopped. The polymer gel was left at room temperature for an additional 60 hr. The polymer slab was broken into smaller pieces and dispersed in 400 mL of deionized water. The resulting suspension was stirred for 2 hr and then filtered. The swollen polymer particles were resuspended in 600 mL of deionized water, stirred for 45 minutes and collected by filtration. The process was repeated with 800 mL of water and 1 hr of stirring. The filtered polymer was dried in a forced air oven at 60° C. to yield 42 g of product.

This procedure results in a polymer which is 4.5 mole percent crosslinked. Similar procedures utilizing appropriate amounts of epichlorohydrin were used to make 3.0, 5.0, 10.0, 15.0, 20.0 and 30.0 mole percent crosslinked gels.

Example 7

Alkylation of Crosslinked Poly(diallylmethylamine) With 1-Bromodecane

The ground polymer (25 g; Example 6) was suspended in 250 mL of deionized water in a 1 L 3-necked round bottom flask. To this swollen gel was added 100 g of 1-bromodecane dissolved in 250 mL of ethanol and the mixture was stirred for 10 minutes. Subsequently, 5 g of 50% aqueous sodium hydroxide was added and the reaction mixture was stirred at room temperature for 40 minutes followed by heating to 75° C. for 1 hr. NaOH solution (2 g) was then added followed by an additional 2 g of NaOH solution after another 1.5 hr. The reaction mixture was stirred at 75° C. for an additional 18 hours, after which time heating was discontinued. After cooling to 30° C., 5 mL of concentrated HCl was added and stirring was continued for 30 minutes. The polymer was filtered and washed with 500 mL of deionized water followed by 500 mL of methanol. Polymer particles were suspended in 600 mL of methanol and stirred for 40 minutes. After removing the solvent by filtration, the polymer was suspended in 500 mL of 2 M NaCl solution and stirred for 40 minutes. The polymer was filtered and the NaCl treatment was repeated two more times. The filtered polymer cake was washed with 500 mL of deionized water and suspended in 500 mL of deionized water. After stirring for 30 minutes the polymer was filtered and resuspended in 700 mL of deionized water and stirred for 30 minutes. Concentrated HCl (2 mL) was added to the suspension and the mixture was stirred for 15 minutes. After stirring for an additional 20 minutes, the polymer was filtered and dried at 60° C. in a forced air oven, yielding 54.6 g of the alkylated polymer as a light yellow solid. The polymer was ground and passed through a 140 mesh sieve.

Example 8

Alkylation of Crosslinked Poly(diallylmethylamine) With 1-Bromododecane

The ground polymer (100 g, Example 6) was suspended in 100 mL of deionized water in a 500 mL 3-neck round-bottom flask. To this swollen gel, 2.8 g of 1-bromodecane dissolved in 100 mL of ethanol was added and the reaction mixture was stirred for 10 minutes. Aqueous sodium hydroxide (2 g; 50% w/w) was then added and the reaction mixture was stirred at room temperature for 40 minutes, followed by heating to 75° C. for 1 hr. NaOH solution (1 g; 50% w/w) was then added followed by an additional 1 g of NaOH solution after another 1.5 hr. The reaction mixture was stirred at 75° C. for an additional 18 h after which time the heating was discontinued. After cooling to 30° C., concentrated HCl (2 mL) was added and the mixture was stirred for 30 minutes. The polymer was filtered and washed with 500 mL of deionized water followed by 500 mL of methanol. Polymer particles were suspended in 300 mL of methanol and stirred for 40 minutes. After removing the solvent by filtration, the polymer was suspended in 500 mL of 2M NaCl solution and stirred for 40 minutes. It was filtered and the NaCl treatment was repeated two more times. The filtered polymer cake was washed with 500 mL of deionized water and suspended in 500 mL of deionized water. After stirring for 30 minutes the polymer was filtered and resuspended in 500 mL of deionized water and stirred for 30 minutes. Concentrated HCl (2 mL) was added to the suspension and the mixture was stirred for 15 minutes. After stirring for an additional 20 minutes, the polymer was filtered and dried at 60° C. in a forced air oven, yielding 18 g of the alkylated polymer as a pale white solid. The polymer was ground and passed through a 140 mesh sieve.

Example 9

Preparation of (3-Chloropropyl) dodecyldimethylammonium Bromide

A 2 L 3-neck round-bottom flask equipped with an air condenser and a magnetic stirrer was charged with N,N-dimethyldodecylamine (297.24 g), 1-bromo-3-chloropropane (220.44 g) and methanol (250 mL). The reaction was maintained at 65° C. for 24 hours. Methanol was removed by rotary evaporation under reduced pressure to yield a brown sludge. To the sludge was added methyl-tert-butylether (2 liters) causing a white solid to form. The mixture was stirred for two hours and a semi-crystalline, white particulate was collected by vacuum filtration. The particulate was dried in a vacuum oven at 35° C. for 24 hours. Yield 228.2 grams (0.61 moles, 44%). (4-Chlorobutyl)dodecyldimethylammonium bromide and (6-chlorohexyl)dodecyldimethylammonium bromide can be prepared by a similar process using the appropriate bromochloroalkane and dodecyldimethylamine.

Example 10

Alkylation of Crosslinked Poly(diallylmethylamine) With (3-Chloropropyl)dimethyldodecylammonium Bromide A mixture of 11 g of crosslinked polymer gel (Example 6) and 74 g of (3-chloropropyl)dimethyldodecylammonium bromide was dispersed in 250 mL of deionized water and heated to 75° C. with stirring. After stirring at 75° C. for minutes, 2 g of a 50% aqueous NaOH solution was added to the reaction mixture. After 2 hr, 1 g of NaOH solution was added followed by an additional 1 g after another 1 hr and the mixture was stirred at 75° C. for 23 hr. The reaction mixture was then allowed to cool. After cooling to 30° C., 3 mL of concentrated HCl was added and the mixture was stirred for 30 minutes. The polymer was filtered and washed with 200 mL of methanol. The filtered polymer particles were dispersed in 400 mL of methanol, stirred for 45 minutes, and filtered. This process was repeated once then the filtered polymer was suspended in 500 mL of 2M NaCl solution, stirred for 45 minutes and filtered. The NaCl treatment was repeated twice and the filtered polymer was suspended in 500 mL of deionized water. The mixture was stirred for 45 minutes, filtered, resuspended in 400 mL of deionized water, and stirred for an additional 40 minutes. To this suspension, 1 mL concentrated HCl was added and the mixture was stirred for 20 minutes. The polymer was filtered and dried in a forced air oven at 60° C., yielding 29 g of alkylated polymer as a light yellow solid which was ground and passed through a 140 mesh sieve.

Example 11

Alkylation of Crosslinked Poly(diallylmethylamine) With (4-Chlorobutyl)dimethyldodecylammonium Bromide A mixture of 10 g of 3% crosslinked polymer gel (Example 6) and 76 g of (4-chlorobutyl) dimethyldodecylammonium bromide was dispersed in 250 mL of deionized water and heated to 70° C. with stirring for 15 minutes. Aqueous NaOH (2 g; 50% w/w) was then added to the reaction mixture. After 2 hr, 1 g of NaOH solution was added followed by additional 1 g after another 2 hr. The reaction mixture was then stirred at 70° C. for 20 hours. Aqueous NaOH (1 g) was then added and the reaction mixture was kept at 70° C. for 20 hr. NaOH solution (1 g) was added and the reaction mixture was kept at 70° C. with stirring for 2 hr. After cooling to 30° C., 2 mL of concentrated HCl was added and the mixture was stirred for 20 minutes. The polymer was filtered and washed successively with 200 mL of deionized water and 200 mL of methanol. The filtered polymer particles were then dispersed in 500 mL methanol, stirred for 30 minutes, and filtered. This process was repeated once and the filtered polymer was suspended in 400 mL of 2M NaCl solution, stirred for 45 minutes and filtered. After repeating NaCl treatment twice, the filtered polymer was suspended in 400 mL of deionized water. The mixture was stirred for 30 minutes, filtered, resuspended in 400 mL of deionized water and stirred for an additional 40 minutes. To this polymer suspension, 1 mL of concentrated HCl was added and the mixture was stirred for 20 minutes. The polymer was then filtered and dried in a forced air oven at 60° C., yielding 27 g of alkylated polymer as a light yellow solid which was ground and passed through a 140 mesh sieve.

Example 12

Alkylation of Crosslinked Poly(diallylmethylamine) With (6-Chlorohexyl)dimethyloctylammonium Bromide A mixture of 10 g of 3% crosslinked polymer gel (Example 6) and 71 g of (6-chlorohexyl) dimethyldodecylammonium bromide was dispersed in 200 mL of deionized water and heated to 75° C. with stirring for 15 minutes. Aqueous NaOH (2 g; 50% w/w) was then added to the reaction mixture. After 3 hr, 1 g of NaOH solution was added. After 2.5 hr an additional 1 g of. NaOH solution was added and the reaction mixture was stirred at 75° C. for 22 hr. Aqueous NaOH (0.5 g) was then added and heating was continued for an additional 2 hr. After cooling to 30° C., 2 mL of concentrated HCl was added and the mixture was stirred for 15 minutes. The polymer was then filtered and washed successively with 200 mL of deionized water and 200 mL of methanol. The filtered polymer particles were then dispersed in 500 mL of methanol, stirred for 30 minutes and filtered. This process was repeated twice, then the filtered polymer was suspended in 400 mL of 2M NaCl solution, stirred for 45 minutes and filtered. After repeating the NaCl treatment twice, the filtered polymer was suspended in 400 mL of deionized water. The mixture was stirred for 30 minutes, filtered, and resuspended in 400 mL of deionized water and stirred for an additional 40 minutes. To this polymer suspension was added 1 mL of concentrated HCl and the mixture was stirred for 20 minutes. The polymer was filtered and dried in a forced air oven at 60° C., yielding 25 g of alkylated polymer as a white solid, which was ground and passed through a 140 mesh sieve.

Example 13

Alkylation of Crosslinked Poly(diallylmethylamine) With 1-Bromodecane

This example illustrates alkylation of the 4.5% crosslinked poly(diallylmethylamine) with different amounts of 1-bromodecane to obtain quaternized polyamines bearing varying amounts of hydrophobic groups. For this purpose, the polymer was treated with varying amounts of 1-bromodecane. Table 1 summarizes amounts of 1-bromodecane used to obtain polymers of varying degree of alkylation and the yield of alkylated polymer.

The 4.5% crosslinked poly(diallylmethylamine)(10 g) was suspended in 150 mL of deionized water. While stirring, 2 g of 50% aqueous NaOH solution was added to the polymer and the suspension was stirred for 15 minutes. At this time an ethanol solution of 1-bromodecane (2.5 mL of ethanol/g 1-bromodecane) was added and the reaction mixture was heated to 75° C. with stirring. After 2 hr, 1 g of aqueous NaOH was added, followed by an additional 1 g of aqueous NaOH after another 2 hr. The reaction mixture was stirred at 75° C. for 18 hours and was then allowed to cool. After cooling to 30° C., 2 mL of concentrated HCl was added and the mixture was stirred for 15 minutes. The polymer was filtered and washed with 200 mL of deionized water and 200 mL of methanol for 30 minutes and filtered. This process was repeated twice and the filtered polymer was suspended in 400 mL of 2M NaCl solution, stirred for 45 minutes and filtered. After repeating the NaCl treatment twice, the filtered polymer was suspended in 400 mL of deionized water. The mixture was stirred for an additional 30 minutes, filtered, resuspended in 400 mL of deionized water and stirred for an additional 40 minutes. To this polymer suspension was added 1 mL of concentrated HCl and the mixture was stirred for 20 minutes. The polymer was filtered, dried in a forced air oven at 60° C., ground and passed through a 140 mesh sieve. Yield of the polymers for different amounts of the 1-bromodecane used are summarized in Table 1.

TABLE 1

Results of the alkylation of 4.5% crosslinked poly(diallylmethylamine) with varying amounts of 1-bromodecane ($C_{10}H_{21}Br$).

| Polymer Used (g) | $C_{10}H_{21}Br$ used (g) | product yield (g) |
| --- | --- | --- |
| 10.0 | 17.0 | 17 |
| 10.0 | 12.5 | 16.8 |
| 10.0 | 8.0 | 14.3 |
| 10.0 | 4.25 | 11.8 |
| 10.0 | 1.70 | 10.6 |

Example 14

Alkylation of Crosslinked Poly(diallylmethylamine) With 1-Bromotetradecane

Ten g of 4.5% crosslinked polydiallylmethylamine (Example 6) was suspended in a 500 mL 3-neck round-bottom flask containing deionized water (100 mL). To this swollen gel was added 32 g of 1-bromotetradecane dissolved in 100 mL ethanol, and the reaction mixture was stirred for 10 minutes. Aqueous sodium hydroxide (2 g, 50% w/w) was then added and the reaction mixture was stirred at room temperature for 40 minutes followed by heating to 75° C. for 1 hr. Aqueous NaOH solution (1 g) was then added followed by an additional 1 g of NaOH solution after another 1.5 hr. The reaction mixture was stirred at 75° C. for an additional 18 hours after which time the heating was discontinued. After cooling to 30° C., 2 mL of concentrated HCl was added and the mixture was stirred for 30 minutes. The polymer was filtered and washed with 500 mL of deionized water followed by 500 mL of methanol. Polymer particles were suspended in 300 mL of methanol and stirred for 40 minutes. After removing the solvent by filtration, the polymer was suspended in 500 mL of 2M NaCl solution and stirred for an additional 40 minutes. The polymer was filtered and this process of NaCl treatment was repeated twice more. The filtered polymer cake was then washed with 500 mL of deionized water and suspended in 500 mL of deionized water. After stirring for 30 minutes the polymer was filtered and resuspended in 500 mL of deionized water and the suspension was stirred for 30 minutes. Concentrated HCl (1 mL) was then added to the suspension, which was stirred for another 55 minutes. The polymer was then filtered and dried at 60° C. in a forced air oven, yielding 22 g of the alkylated polymer. The polymer was ground and passed through a 140 mesh sieve.

Example 15

Alkylation of Crosslinked Poly(diallylmethylamine) With 1-Bromooctane

Ten g of 4.5% crosslinked poly(diallylmethylamine) (Example 6) was suspended in a 500 mL 3-neck round bottom flask containing deionized water (100 mL). To this swollen gel was added 23 g of 1-bromooctane dissolved in 100 mL of ethanol and the reaction mixture was stirred for 10 minutes. Aqueous sodium hydroxide (2 g; 50% w/w) was then added and the reaction mixture was stirred at room temperature for 40 minutes, followed by heating to 75° C. for 1 hr. NaOH solution (1 g) was then added, followed by an additional 1 g of NaOH solution after another 1.5 hr. The reaction mixture was allowed to stir at 75° C. for an additional 18 hours after which time the heating was discontinued. After cooling to 30° C., 2 mL of concentrated HCl was added and stirring was continued for 30 minutes. The polymer was filtered and washed with 500 mL of deionized water followed by 500 mL of-methanol. Polymer particles were suspended in 300 mL of methanol and stirred for 40 minutes. After removing the solvent by filtration, the polymer was suspended in 500 mL 2M of NaCl solution and the suspension was stirred for 40 minutes. The polymer was filtered and this process of NaCl treatment was repeated twice more. The filtered polymer cake was washed with 500 mL deionized water and suspended in 500 mL of deionized water. After stirring for 30 minutes the polymer was filtered, resuspended in 500 mL of deionized water, and stirred for 30 minutes. Concentrated HCl (1 mL) was added to the suspension and stirred for 35 minutes. The polymer was then filtered and dried at 60° C. in a forced air oven, yielding 15.8 g of the alkylated polymer. The polymer was ground and passed through a 140 mesh sieve.

Example 16

Alkylation of Crosslinked Poly(diallylmethylamine) With 1-Bromohexane

Ten g of 4.5% crosslinked poly(diallylmethylamine) (Example 6) was suspended in deionized water (100 mL) in a 500 mL 3-neck round bottom flask. To this swollen gel was added 19 g of 1-bromodecane dissolved in 100 mL of ethanol, and the reaction mixture was stirred for 10 minutes. Aqueous sodium hydroxide (2 g; 50% w/w) was then added and the reaction mixture was stirred at room temperature for 40 minutes, followed by heating to 75° C. for 1 hr. Additional NaOH solution (1 g) was then added, followed by an additional 1 g of NaOH solution after another 1.5 hr. The reaction mixture was stirred at 75° C. for an additional 18 hours after which time the heating was discontinued. After cooling to 30° C., 2 mL of concentrated HCl was added and the mixture was stirred for 30 minutes. The polymer was filtered and washed with 500 mL of deionized water followed by 500 mL of methanol. The polymer particles were suspended in 300 mL of methanol and stirred for 40 minutes. After removing the solvent by filtration, the polymer was suspended in 500 mL of 2 M NaCl solution and the suspension was stirred for 40 minutes. The polymer was filtered and this process of NaCl treatment was repeated twice more. The filtered polymer cake was washed with 500 mL of deionized water and suspended in 500 mL of deionized water. After stirring for 30 minutes, the polymer was filtered, resuspended in 500 mL of deionized water and stirred for 30 minutes. Concentrated HCl (1 mL) was added to the suspension, which was stirred for 35 minutes. The polymer was then filtered and dried at 60° C. in a forced air oven, yielding 13.7 g of the alkylated polymer. The polymer was ground and passed through a 140 mesh sieve.

Example 17

Synthesis of Quaternized N-Alkyl Diallylmethylammonium Salts

Synthesis of N-Decyldiallylmethylammonium Bromide

Diallylmethylamine (33.3 g) and 1-bromodecane (66.6 g) were dissolved in 100 mL of methanol and the reaction mixture was stirred at 65° C. for 48 hours. After cooling to room temperature, the methanol was removed under reduced pressure. The residual viscous oil was precipitated into 800 mL of ether with rapid stirring. The ether layer was decanted and the residue was again treated with 500 mL of ether. After stirring for 15 minutes the solvent was removed and the oily residue was dried under vacuum at 35° C. for 48 hours, yielding 78 g of the product.

Synthesis of N-(N,N-Dimethyl-N-dodecylammonio) propyldiallylmethylammonium Chloride Bromide A mixture of 22 g of diallylmethylamine and 74 g 3-chloropropyldodecyldimethylammonium bromide was dissolved in 100 mL of methanol and the reaction mixture was stirred at 65° C. for 48 hours. After cooling to room temperature, the solvent was removed under reduced pressure. The residual viscous oil was precipitated into 800 mL of ether with rapid stirring. The ether layer was decanted and the residue was again treated with 500 mL of ether. After stirring for 15 minutes the solvent was removed and the oily residue was dried under vacuum at 35° C. for 48 hours, yielding 70 g of the product.

Synthesis of N-(N,N-Dimethyl-N-dodecylammonio) butyldiallylmethylammonium Chloride Bromide A mixture of 22 g of diallylmethylamine and 75 g 4-chlorobutyldimethyldodecylammonium bromide was dissolved in 100 mL of methanol and the reaction mixture was stirred at 65° C. for 48 hours. After cooling to room temperature, the solvent was removed under reduced pressure. The residual viscous oil was precipitated into 800 mL of ether with rapid stirring. The ether layer was decanted and the residue was again treated with 500 mL of ether. After stirring for 15 minutes the solvent was removed and the oily residue was dried under vacuum at 35° C. for 48 hours, yielding 65 g of the product.

Example 18

Synthesis of Poly(N-decyldiallylmethylammonium Bromide) Crosslinked With Methylenebis (acrylamide)

N-decyldiallylmethylammonium bromide (25 g), 3 g N,N-methylenebisacrylamide (3 g) and 2,2'-azobis(2-amidinopropane)dihydrochloride (300 mg) were dissolved in 100 mL of deionized water. The solution was bubbled with a slow stream of nitrogen for 30 minutes then heated to 70° C. with stirring. After 2 hr, the reaction mixture turned cloudy with formation of a suspension. The mixture was kept at 70° C. for a period of 18 hours and then allowed to cool. The suspension was centrifuged. The residue was dispersed in 200 mL of deionized water, stirred for 30 minutes and centrifuged. After removal of the supernatant, the residue was suspended in 200 mL of methanol, stirred for 30 minutes and centrifuged. The residue was suspended in 300 mL of methanol and the suspension was refluxed for 1 hr. After cooling to room temperature, the suspension was filtered and the white solid was dried at 60° C. for 24 hr to yield 10 g of product. The polymer was ground and passed through 140 mesh sieve.

Example 19

Synthesis of 6% Crosslinked Poly (diallylammonium Chloride-co-sulfur Dioxide) Copolymer A 20% solution of copoly(diallylmethylammonium chloride-co-sulfur dioxide) (Nitto Boseki Co.; 111 g pf 2-% solution) was treated with 2.2 g of solid NaOH with stirring. The bottom viscous layer was separated from the top layer and the former was diluted with 20 mL of water. To this solution, 0.6 mL of epichlorohydrin was added and the reaction mixture was allowed to stir for 2 hr. The reaction medium was left at room temperature for 48 hours, during which period it turned into a gel. The resulting polymer gel was broken into smaller pieces and was dispersed in 1 liter deionized water. The suspension was stirred for 1 hr and filtered. The swollen polymer particles were resuspended in 800 mL of deionized water and stirred for 1.5 hr. The polymer particles were then filtered and dried in a forced air oven at 60° C. to yield 16 g of polymer. The dried polymer was ground and passed through a 10 mesh sieve.

Example 20

Alkylation of 6% Crosslinked Copoly (diallylmethylamine-co-sulfur Dioxide) With 1-Bromodecane The polymer of Example 19 (5 g) was placed in a 500 mL 3-neck round bottom flask and suspended in 100 mL of deionized water. To this swollen gel was added a solution of 18 g of 1-bromodecane in 100 mL of ethanol and the reaction mixture stirred for 10 minutes. Subsequently, 2 g of 50% aqueous sodium hydroxide was added and the reaction mixture was stirred at room temperature for 30 minutes followed by heating to 75° C. After 1 hr, 0.5 g of NaOH solution was added followed by an additional 0.5 g of NaOH solution after another 1.5 hr. The reaction mixture was allowed to stir at 75° C. for an additional 18 hr after which time the heating was discontinued. After cooling to 30° C., 2 mL of concentrated HCl was added and the mixture was stirred for 30 minutes. The polymer was filtered off and washed with 500 mL of deionized water and 500 mL of methanol. Polymer particles were suspended in 300 mL of methanol and stirred for 40 minutes. After removing the solvent by filtration, the polymer was suspended in 500 mL of 2M NaCl solution and stirred for 40 minutes. The suspension was filtered and the NaCl treatment was repeated two more times. The filtered polymer cake was washed with 500 mL of deionized water and suspended in 500 mL of deionized water. After stirring for 30 minutes it was filtered and resuspended in 500 mL of deionized water and stirred for 30 minutes. Concentrated HCl (1 mL) was added to the suspension and the suspension was stirred for 35 minutes. The polymer was then filtered and dried at 60° C. in a forced air oven, yielding 9.1 g of the alkylated polymer. The polymer was ground and passed through a 140 mesh sieve.

Example 21

Alkylation of Crosslinked Copoly (diallylmethylamine-co-sulfur Dioxide) With (3-Chloropropyl)-dimethyldodecylammonium Bromide To a mixture of 5 g of the polymer of Example 19 and 30 g of (3-chloropropyl)dimethyldodecylammonium bromide in a 500 mL 3-necked round bottomed flask was added 150 mL of deionized water. Aqueous sodium hydroxide (2 g of 50% w/w) was added and the reaction mixture was stirred at room temperature for 30 minutes, followed by heating to 75° C. for 1 hr. NaOH solution (0.5 g) was added, followed by an additional 0.5 g of NaOH solution after another 1.5 hr. The reaction mixture was allowed to stir at 75° C. for an additional 18 hr after which time the heating was discontinued. After cooling to 30° C., 2 mL of concentrated HCl was added and the mixture was stirred for 30 minutes. The polymer was filtered off and washed with 500 mL of deionized water and 500 mL of methanol. Polymer particles were then suspended in 300 mL of methanol and the suspension was stirred for 40 minutes. The polymer was isolated by filtration and then suspended in 500 mL of 2M NaCl solution. The suspension was stirred for 40 minutes. The polymer was filtered off and this NaCl treatment was repeated two more times. The filtered polymer cake was washed with 500 mL of deionized water and then suspended in 500 mL of deionized water. After stirring for 30 minutes the polymer was filtered off and resuspended in 500 mL deionized water. The suspension was stirred for 30 minutes. Concentrated HCl (1 mL) was added and the suspension was stirred for 35 minutes. The polymer was then filtered and dried at 60° C. in a forced air oven, yielding 11.4 g of the alkylated polymer. The polymer was ground and passed through a 140 mesh sieve.

Example 22

Preparation of Poly(diallylammonium Chloride)

Diallylamine (100 g) and 100 mL of deionized water were placed in a 1-liter beaker and the mixture was allowed to stir. To this stirred mixture, 37% aqueous HCl was added slowly with concurrent measurement of pH. When the pH of the solution dropped below 7, addition of acid was stopped. The solution was extracted with 600 mL diethyl ether. To the aqueous solution, 3 g of 2,2'-azobis(2-amidinopropane) dihydrochloride was added and the solution was bubbled with nitrogen gas for 45 minutes. The solution was then heated to 70° C. for 48 hr. Heating was discontinued and, after cooling to room temperature, 315 g of polymer solution was obtained.

Example 23

Synthesis of Insoluble Crosslinked Polydiallylamine

The polydiallylammonium chloride solution of Example 22 (150 g) was diluted with 50 mL of deionized water. Solid NaOH (6.75 g) was added to the polymer solution with stirring. The reaction mixture was stirred until the NaOH had dissolved and the temperature of the solution had dropped to below 30° C. To this partially neutralized polymer solution, epichlorohydrin (1.2 mL) was added and stirring was continued. The reaction medium slowly became increasingly viscous and after about 50 minutes it gelled and the stirring was stopped. This gelled polymer was left at room temperature for an additional 48 hr. The polymer slab was broken into smaller pieces and was dispersed in 1 L of deionized water. The resulting suspension was stirred for 1.5 hr and then filtered. The swollen polymer particles were resuspended in 1 L of deionized water and the suspension was stirred for 40 minutes. The polymer particles were filtered off and dried in a forced air oven at 60° C. to yield 56 g of pale white solid polymer. The dried polymer was ground and passed through a 10 mesh sieve.

Example 24

Alkylation of Crosslinked Polydiallylamine With 1-Bromododecane

The ground polymer of Example 23 (5 g) was placed in a 500-mL 3-neck round-bottom flask and suspended in 100 mL of deionized water. The suspension was stirred with a mechanical stirrer. To this swollen gel was added a solution of 15 g of 1-bromodecane in 100 mL of ethanol, and the reaction mixture was stirred for 10 minutes. Aqueous sodium hydroxide (2 g of 50% w/w) was then added and the reaction mixture was stirred at room temperature for 40 minutes followed by heating to 75° C. Subsequently, an additional 4 g of 50% NaOH was added in 1 g batches at an interval of 1.5 hr. The reaction mixture was allowed to stir at 75° C. for a total period of 20 hr. After cooling to 30° C., 2 mL concentrated HCl was added and the mixture was stirred for 30 minutes. The polymer was filtered off and washed with 500 mL of deionized water and 500 mL of methanol. The filtered polymer particles were slurried in methanol (400 mL), stirred for 40 minutes, and reisolated by filtration. This process was then repeated. The polymer was suspended in 500 mL of 2M NaCl solution and the suspension was stirred for 40 minutes. The polymer was filtered off and this NaCl treatment was repeated two more times. The fitered polymer cake was washed with 500 mL of deionized water and suspended in 500 mL of deionized water. After stirring the suspension for 30 minutes, the polymer was filtered off and resuspended in 500 mL of deionized water. The resulting suspension was stirred for 30 minutes. Concentrated HCl (1 mL) was added to the suspension, which was then stirred for 35 minutes. The polymer was then filtered off and dried at 60° C. in a forced air oven, yielding 13.3 g of the alkylated polymer as a pale white solid. The polymer was ground and passed through a 140 mesh sieve.

Example 25

Alkylation of Crosslinked Polydiallylamine With (3-Chloropropyl)dimethyldodecylammonium Bromide A mixture of 5 g of the crosslinked polymer gel of Example 23 and 28 g of (3-chloropropyl)

dimethyldodecylammonium bromide was dispersed in 150 mL of deionized water and the suspension was stirred. To this suspension was added aqueous NaOH (2 g of 50% w/w), and the mixture was stirred for 15 minutes. The mixture was then heated with stirring to 75° C. An additional 4 g of 50% NaOH was added in 1 g batches at 1.5 hr intervals. After stirring at 75° C. for a total period of 18 hr, the reaction mixture was allowed to cool. After cooling to 30° C., 2 mL of concentrated HCl was added and the mixture was stirred for 30 minutes. The polymer particles were filtered off and washed with 200 mL of methanol. The filtered polymer particles were suspended in methanol (400 mL) and the suspension was stirred for 40 minutes followed by filtration. This rinsing was repeated two more times with methanol (400 mL). After removing the polymer by filtration, the polymer was suspended in 500 mL of 2M NaCl solution and the suspension was stirred for 40 minutes, followed by filtration. This NaCl treatment was repeated twice more and the filtered polymer was suspended in 500 mL deionized waer. The mixture was stirred for an additional 45 minutes, filtered, resuspended in 400 mL deionized water and stirred for another 40 minutes. To this suspension, 1 mL concentrated HCl was added and the mixture was stirred for 20 minutes. The polymer was filtered off and dried in a forced air oven at 60° C., yielding 13.2 g of alkylated polymer as a light yellow solid which was ground and passed through a 140 mesh sieve.

Example 26

Alkylation of Crosslinked Poly(diallylmethylamine) With 1-Bromooctane

The 3% crosslinked poly(diallylmethylamine) of Example 6 (5 g) was taken in a 500-mL 3-neck round-bottom flask and suspended in 110 mL of deionized water. To this swollen gel was added a solution-of 11.1 g 1-bromooctane in 50 mL ethanol and the reaction mixture was stirred for 10 minutes. Aqueous sodium hydroxide (1 g of 50% w/w) was then added and the reaction mixture was stirred at room temperature for 40 minutes followed by heating to 75° C. for 1.5 hr. NaOH solution (1 g) was added, and the reaction mixture was allowed to stir at 75° C. for an additional 18 hr. After the mixture had cooled to 30° C., 2.5 mL of concentrated HCl was added and the mixture was stirred for 30 minutes. The polymer was filtered and washed with 300 mL of deionized water and 300 mL of methanol. The polymer particles were suspended in 300 mL of methanol and the suspension was stirred for 40 minutes. After removing the polymer by filtration, the polymer was suspended in 300 mL of 2 M NaCl solution and the suspension was stirred for 40 minutes. The polymer was filtered off and this NaCl treatment was repeated two more times. The filtered polymer cake was washed with 400 mL of deionized water, then suspended in 400 mL of deionized water. After the suspension was stirred for 30 minutes, it was filtered and the polymer was resuspended in 400 mL of deionized water and this suspension was stirred for an additional 30 minutes. Concentrated HCl (1 mL) was added to the suspension, which was then stirred for 30 minutes. The polymer was filtered and dried at 60° C. in a forced air oven, yielding 7.0 g of the alkylated polymer as a pale white solid. The polymer was ground and passed through a 140 mesh sieve.

Example 27

Alkylation of Crosslinked Poly(diallylmethylamine) With 1-Bromotetradecane

The 3% crosslinked poly(diallylmethylamine) of Example 6 (5 g) was taken in a 500-mL 3-neck round bottom flask and suspended in 100 mL of deionized water. To this swollen gel was added 16 g 1-bromotetradecane dissolved in 40 mL ethanol. The reaction mixture was stirred for 10 minutes. Aqueous sodium hydroxide (1 g of 50% w/w) was then added and the reaction mixture was stirred at room temperature for 40 minutes followed by heating to 75° C. for 1.5 hr. NaOH solution (1 g of 50% w/w) was then added and the reaction mixture was stirred at 75° C. for additional 18 hr. After cooling to 30° C., 2.5 mL of concentrated HCl was added and the mixture was stirred for 30 minutes. The polymer was filtered and washed with 300 mL of deionized water and 300 mL of methanol. The polymer particles were suspended in 300 mL of methanol and the suspension was stirred for 40 minutes. After removing the polymer by filtration, the polymer was suspended in 300 mL of 2M NaCl solution and the suspension was stirred for 40 minutes. The polymer was filtered off and this NaCl treatment was repeated two more times. The filtered polymer cake was washed with 400 mL of deionized water and suspended in 400 mL of deionized water. After stirring for 30 minutes the suspension was filtered and the polymer was resuspended in 400 mL of deionized water. This suspension was stirred for an additional 30 minutes. Concentrated HCl (1 mL) was then added to the suspension and stirring continued for 30 minutes. The polymer was filtered off and dried at 60° C. in a forced air oven, yielding 9.0 g of the alkylated polymer as a pale white solid. The polymer was ground and passed through a 140 mesh sieve.

Example 28

Alkylation of Crosslinked Poly(diallylmethylamine) With (3-Chloropropyl)dimethyloctadecylammonium Bromide (3-Chloropropyl)dimethyloctadecylammonium bromide was prepared by the general method of Example 9 starting with dimethyloctadecylamine. A mixture of the crosslinked polymer gel of Example 6 and 35 g (3-chloropropyl) dimethyloctadecylammonium bromide was dispersed in 150 mL of deionized water and the mixture was heated to 70° C. with stirring for 15 minutes. Aqueous NaOH (2 g of 50% w/w) and 50 mL ethanol were then added to the reaction mixture. After 2 hr, 0.5 g of NaOH solution (50% w/w) was added and the reaction mixture was stirred at 70° C. for 20 hr. When the reaction mixture had cooled to 30° C., 2 mL of concentrated HCl was added and the mixture was stirred for another 20 minutes. The polymer was filtered off and washed with 200 mL of deionized water and 200 mL of methanol. The filtered polymer particles were dispersed in 500 mL of methanol, stirred for another 30 minutes and then filtered. This methanol rinse process was repeated one more time and the filtered polymer was suspended in 300 mL of 2M NaCl solution. The resulting suspension was stirred for another 45 minutes and filtered. After repeating the NaCl treatment twice more, the filtered polymer was suspended in 400 mL of deionized water. The mixture was stirred for 30 minutes, filtered, and the polymer was resuspended in 400 mL of deionized water. The suspension was stirred for an additional 40 minutes. To this suspension was added 1 mL of concentrated HCl and the mixture was stirred for 20 minutes. The polymer was filtered and dried in a forced air oven at 60° C., yielding 10.7 g alkylated polymer as a pale white solid which was ground and passed through a 140 mesh sieve.

Example 29

Alkylation of Crosslinked Poly(diallylmethylamine) With (3-Chloropropyl)dodecylpyrrolidinium Bromide Synthesis of (3-Chloropropyl)dodecylpyrrolidinium Bromide Pyrrolidine (47 g), 1-bromododecane (149.5 g) and potassium carbonate (83 g) were added to 560 mL of acetone. The reaction mixture was heated to 55° C. for 24 hr. then filtered. Solvent was removed from the filtrate, yielding 92 g of N-dodecylpyrrolidine. N-dodecylpyrrolidine (80 g) and 1-bromo-3-chloropropane (52.6 g) were dissolved in 133 mL of methanol and the reaction mixture was heated to 65° C. for 18 hr. After cooling to room temperature, methanol was removed under reduced pressure. The residue was poured into 2 L of diethylether with stirring and the mixture was allowed to stand for another 6 hr. The white precipitate was filtered and dried at 40° C. under a vacuum for 24 hr yielding 85 g of (3-chloropropyl)dodecylpyrrolidinium bromide as a white solid.

Alkylation of Crosslinked Poly(diallylmethylamine) With (3-Chloropropyl)dodecylpyrrolidinium Bromide The 3% crosslinked poly(diallylmethylamine) of Example 6 (5 g) and (3-chloropropyl)dodecylpyrrolidinium bromide (30 g) were dispersed in 150 mL of deionized water and the mixture was heated to 70° C. with stirring. After stirring at 70° C. for 15 minutes, 2 g of 50% aqueous NaOH was added to the reaction mixture. After 2 hr, 1 g of 50% aqueous NaOH solution was added and the reaction mixture was allowed to stir at 70° C. for 20 hr. The reaction mixture was then allowed to cool to 30° C. Concentrated HCl (2 mL) was then added and the mixture was stirred for 20 minutes. The polymer was filtered off and washed with 200 mL of deionized water and 200 mL of methanol. The polymer particles were dispersed in 500 mL of methanol and the suspension was stirred for 30 minutes and then filtered. This process was repeated one more time and the filtered polymer was suspended in 300 mL of 2M NaCl solution. The resulting suspension was stirred for 45 minutes and filtered. After repeating this NaCl treatment twice more, the filtered polymer was suspended in 400 mL of deionized water. The mixture was stirred for 30 minutes, filtered, resuspended in 400 mL deionized water and stirred for an additional 40 minutes. To this polymer suspension was added 1 mL of concentrated HCl and stirring continued for an additional 20 minutes. The polymer was filtered off and dried in a forced air oven at 60° C., yielding 13 g of alkylated polymer as a pale white solid which was ground and passed through a 140-mesh sieve.

Example 30

Alkylation of Crosslinked Poly(diallylmethylamine) With (3-Chloropropyl)dodecylpiperidinium Bromide Synthesis of (3-Chloropropyl)decylpiperidinium Bromide N-decylpiperidine was synthesized by reacting 45.7 g of piperidine with 118.7 g of 1-bromodecane in 237 mL of acetone in the presence of 74 g of potassium carbonate. After refluxing this reaction mixture at 55° C. for 24 hr, it was filtered and acetone was removed from the filtrate to yield 61 g of N-decylpiperidine. N-decylpiperidine (5 g) and 42 g of 1-bromo-3-chloropropane were dissolved in 50 mL of methanol and the reaction mixture was heated to 65° C. for 18 hr. After cooling to room temperature, methanol was removed under reduced pressure. The residue was poured into 2 L of tert-butylmethyl ether with stirring and then the mixture was allowed to stand for 6 hr. The white precipitate was collected by filtered and was dried at 400 C under vacuum for 24 hr yielding 68 g of (3-chloropropyl) decylpiperidinium bromide as a light yellow solid.

Alkylation of Crosslinked Poly(diallylmethylamine) With (3-Chloropropyl)decylpiperidinium Bromide The 3% crosslinked poly(diallylmethylamine) of Example 6 (5 g) and 32 g of (3-chloropropyl) decylpiperidinium bromide were dispersed in 150 mL of deionized water and the reaction mixture was heated to 70° C. with stirring for 15 minutes. Aqueous NaOH (2 g of 50% w/w) was then added to the reaction mixture. After 2 hr, 1 g of NaOH solution (50% w/w) was added and the reaction mixture was allowed to stir at 70° C. for 20 h. When the reaction mixture had cooled to 30° C., 2 mL of concentrated HCl was added, and the mixture was stirred for 20 minutes. The polymer was collected by filtration and washed with 200 mL of deionized water and 200 mL of methanol. The polymer particles were dispersed in 500 mL of methanol and the suspension was stirred for an additional 30 minutes, then filtered. This methanol rinse process was repeated once and the polymer was suspended in 300 mL of 2M NaCl solution. The suspension was stirred for 45 minutes and filtered. After repeating this NaCl treatment twice more, the filtered polymer was suspended in 400 mL of deionized water. The mixture was stirred for 30 minutes, filtered, resuspended in 400 mL of deionized water and the suspension was stirred for 40 minutes. To this polymer suspension was added 1 mL of concentrated HCl and the mixture was stirred for 20 minutes. The polymer was collected by filtration and dried in a forced air oven at 60° C., yielding 13.2 g alkylated polymer as a pale white solid which was ground and passed through a 140-mesh sieve.

Example 31

Alkylation of Crosslinked Poly(diallylmethylamine) With (4-Chlorobutyl)diethyldecylammonium Bromide (4-Chlorobutyl)diethyldecylammonium bromide was prepared by the general method of Example 9 using 4-chloro-1-bromobutane and decyldiethylamine. The 3% crosslinked poly(diallylmethylamine) of Example 6 (5 g) and 22 g (4-chlorobutyl)diethyldecylammonium bromide were dispersed in 150 mL of deionized water. The resulting mixture was heated to 70° C. with stirring for 15 minutes. Aqueous NaOH (2 g of 50% w/w) was then added to the reaction mixture. After 2 hr, 0.5 g of NaOH solution (50% w/w) was added and the reaction mixture was allowed to stir at 70° C. for 20 hr. When the reaction mixture had cooled to 30° C., 2 mL of concentrated HCl was added and the mixture was stirred for an additional 20 minutes. The polymer was filtered off and washed with 200 mL of deionized water and 200 mL of methanol. The polymer particles were dispersed in 500 mL of methanol and the suspension was stirred for 30 minutes, then filtered. This process was repeated once and the filtered polymer was suspended in 300 mL of 2M NaCl solution. The suspension was stirred for an additional 45 minutes and filtered. After repeating this NaCl treatment twice more, the filtered polymer was suspended in 400 mL of deionized water and the mixture was stirred for an additional 40 minutes. To this polymer suspension was added 1 mL of concentrated HCl and the mixture was stirred for 20 minutes. The polymer was filtered off and dried in a forced air oven at 60° C., yielding 10.6 g of alkylated polymer as a pale white solid which was ground and passed through a 140 mesh sieve.

Example 32

Alkylation of Crosslinked Poly(diallylmethylamine) With Varying Amounts of (3-Chloropropyl) dimethyldodecylammonium Bromide This example illustrates alkylation of the 3% crosslinked poly(diallylmethylamine) of Example 6 with different amounts of (3-chloropropyl)dimethyldodecylammonium bromide. For this purpose, the polymer was treated with varying amounts of the alkylating agent via the general procedure described in Example 10. Table 2 summarizes amounts of (3-chloropropyl)dimethyldodecylammonium bromide used to obtain polymers of varying degree of alkylation.

TABLE 2

Results of the alkylation of 3% crosslinked poly(diallylmethylamine) with varying amounts of (3-chloropropyl) dimethyldodecylammonium bromide.

| Polymer used (grams) | alkylating agent used (grams) | Yield of alkylated polymer (in grams) |
|---|---|---|
| 5.0 | 14.25 | 11.3 |
| 5.0 | 10.7 | 8.3 |
| 5.0 | 7.1 | 7.0 |
| 5.0 | 3.6 | 6.0 |
| 5.0 | 1.40 | 5.1 |

Example 33

Synthesis of 1,4-Butanediol Diglycidyl Ether Crosslinked Poly(diallylmethylamine)

A 60% solution of poly(diallylmethylamine) (33.2 g of 60% solution w/w) was diluted with 68 mL of deionized water. While stirring, 2.8 g of NaOH was added to the polymer solution. The reaction mixture was allowed to stir until all NaOH had dissolved. When the temperature of the solution dropped to below 30° C., 1.25 g of 1,4-butanediol diglycidyl ether was added and stirring continued. The reaction medium slowly became increasingly viscous and after about 45 minutes it gelled and the stirring was stopped. The polymer gel was left at room temperature for an additional 48 hours. The polymer slab was broken into smaller pieces and was dispersed in 300 mL of deionized water. The suspension was stirred for 30 minutes and was filtered. The swollen polymer particles were resuspended in 400 mL of deionized water, stirred for 1 hr and filtered. This process was repeated twice more. The filtered polymer (swollen gel) was dried in a forced air oven at 60° C. to yield 15 g of the product.

Example 34

Alkylation of 1,4-Butanediol Diglycidyl Ether-crosslinked Poly(dialiylmethylamine) With 1-Bromodecane Crosslinked poly(diallylmethylamine) (Example 33; 5 g) was placed in a 500 mL 3-necked round-bottomed flask and suspended in 100 mL of deionized water. To this swollen gel was added 12 g of 1-bromodecane dissolved in 100 mL ethanol, and the reaction mixture was stirred for 10 minutes. Subsequently, 1 g of 50% (w/w) aqueous sodium hydroxide was added and the reaction mixture was stirred at room temperature for 40 minutes followed by an additional 0.5 g of NaOH solution after another 1.5 hr. The reaction mixture was allowed to stir at 75° C. for an additional 18 hrs after which time heating was discontinued. After cooling to 30° C., 2 mL of concentrated HCl was added and stirring was continued for 30 minutes. The polymer was filtered and washed with 250 mL of deionized water followed by 250 mL of methanol. The polymer particles were suspended in 300 mL of methanol and stirred for 40 minutes. After removing the solvent by filtration, the polymer was suspended in 250 mL 2M of NaCl solution and stirred for an additional 40 minutes. The solid was collected by filtration, and this process of NaCl treatment was repeated two more times. The filtered polymer cake was washed with 250 mL deionized water and suspended in 250 mL of deionized water. After stirring for 30 minutes it was filtered and resuspended in 400 mL of deionized water, and stirred for an additional 30 minutes. Concentrated HCl (2 mL) was added to the suspension and stirred for another 15 minutes. After stirring for an additional 20 minutes, the polymer was filtered and dried at 60° C. in a forced air oven yielding 9 g of the alkylated polymer as a pale white solid. The polymer was ground and passed through a 140 mesh sieve.

Example 35

A solution of allylammonium chloride (25.0 g of a 60% aqueous solution), diallylammonium chloride (66.81 g of a 67% aqueous solution), triallylammonium chloride (40.87 g of a 68% aqueous solution), and 2,2'-azobis(2-amidinopropane) dihydrochloride (4.28 g of a 20% aqueous solution), was heated at 55° C. under a nitrogen atmosphere for 18 h and then at 80° C. for 2 h. After cooling to room temperature, the solution was precipitated from isopropanol (1 L). After stirring for 20 min, and decanting the isopropanol layer, the polymer was stirred again with isopropanol (1 L). After decanting the isopropanol, and drying in the oven, 45.1 g of solid was isolated.

A portion of this polymer (20 g) dissolved in water (80 mL), was treated with NaOH (1.6 g of a 50% aqueous solution) and epichlorohydrin (1.17 mL). After mixing, the solution was allowed to stir at room temperature overnight. The resulting gel was suspended in water (2 L) and concentrated HCl (2 mL) was added. After filtration, the polymer was dried in a 65° C. forced-air oven to give 5.6g of solid.

Example 36

Preparation of Crosslinked Poly(diallylamine)

Concentrated hydrochloric acid (1521.0 g; 37% was charged to a 5 L jacketed reaction kettle and agitated with a mechanical stirrer. The reaction was cooled to <0° C. with circulating coolant. Diallylamine (1500.0 g) was added dropwise to the stirring hydrochloric acid over an 8-hour period using an addition funnel capped with a pierced rubber septum. The stirring solution temperature was maintained at <10° C. After the addition was completed, the mixture was allowed to warm to room temperature. An additional 125.0 g of concentrated hydrochloric acid was added. Isopropanol (790.0 g) was added, and the stirring solution was purged with nitrogen gas while heating to 60° C. for approximately 2 hours. Once the solution reached 60° C., the purging was stopped and a nitrogen blanket was maintained over the reaction mixture. 2,2'-Azobis[2-amidinopropane] dihydrochloride (15.0 g) was added as a 20% aqueous solution. The solution was heated at 60–62° C. for 24 hours. A second portion of 2,2'-azobis[2-amidinopropane] dihydrochloride (15.0 g) was added as a 20% aqueous solution, and the solution was heated at 60–62° C. for an additional 24 hours. A third portion of 2,2'-Azobis[2-amidinopropane] dihydrochloride (15.0 g) was added as a 20% aqueous solution, and the solution was heated at 60–62° C. for a final 24 hours, then cooled to room temperature. The polymer solution was drained from the reactor and prepared as described below for crosslinking with epichlorohydrin.

The polymer solution (2473.4 g) was diluted with 8092.3 g deionized water. The mixture was stirred vigorously. Solid sodium hydroxide (412 g) was added and the mixture stirred vigorously until the sodium hydroxide pellets were completely dissolved. Epichlorohydrin (292.7 g) was added and the mixture was stirred vigorously for 16 minutes. Stirring was stopped and the mixture was covered. The gel was allowed to cure for 18 hours. The solid gel was then ground using a Kitchen Aid food grinder. The ground polymer was washed in two portions on a large plastic Buchner funnel lined with filter paper. A second piece of filter paper, perforated with holes, was placed on top of each polymer cake to prevent disturbing the cake when adding wash water. Fresh deionized $H_2O$ was added to the top of the cake and drained under vacuum. When the filter effluent had a conductivity of less than 2 mS/cm, the wet polymer was washed in portions as a water slurry in a large plastic bucket. Water was added to each slurried portion until the stirring conductivity was 0.5 mS/cm. The portions were then recombined and filtered in two large plastic Buchner funnels. The filtered polymer was transferred to glass drying trays and dried in a 60° C. forced air oven for several days. The final dry weight was 1331.5 g.

Example 37

Suspension Copolymerization of Diallylamine and Triallylamine

A solution of 39.3 g of an aqueous solution (68 wt %) of diallylamine hydrochloride, 5.3 g of an aqueous solution (73 wt %) of triallylamine hydrochloride and 0.9 g of 2,2'-Azobis(2-amidinopropane) dihydrochloride was bubbled with a slow stream of nitrogen for 30 minutes. While stirring, this reaction mixture was added to a solution of 7 g of polyvinylacetate in 300 mL of toluene. The resulting mixture was stirred at room temperature for 45 minutes under a nitrogen atmosphere. While stirring, the temperature of the reaction mixture was raised to 60° C. and was held at this temperature for 24 hr. The reaction mixture was allowed to cool to room temperature and the polymer particles were collected by filtration. While in the funnel, the filtered particles were successively washed with 300 mL of toluene and 500 mL of methanol. The polymer particles were suspended in 500 mL of methanol, stirred for 50 minutes, and filtered. Subsequently, the particles were suspended in 400 mL of deionized water, stirred for 30 minutes, and filtered. The filtered particles were dried at 60° C. for 24 hr to yield 15 g of the polymer.

Example 38

Preparation of Copoly(diallylpyrrolidinium Chloride/1,6-bis(diallylmethylammonium Chloride) hexane)

A solution of diallylpyrrolidinium bromide (10.0 g), 1,6-bis(diallymethylammonium bromide)hexane (4.01 g), 2,2'-azobis(2-amidinopropane) dihydrochloride (0.10 g dissolved in 4 drops of water) and methanol (10 mL) was heated at 60° C. under a nitrogen atmosphere for 12 hr. The resulting material was washed with MeOH (3×500 mL), and then washed with 2M NaCl (3×500 mL), and then with water (2.0 L). The polymer was then suspended in water (1 L) and this suspension was acidified with conc Hcl to pH 2.6. After filtration, the polymer was dried at 60° C. in a forced-air oven to give 7.1 g of a solid.

Example 39

Preparation of Copoly(diallylpyrrolidinium Chloride/Ethylenebisacrylamide)

A solution of diallylpyrrolidinium bromide (10.0 g), ethylenebisacrylamide (1.45 g), 2,2'-azobis(2-amidinopropane) dihydrochloride (0.10 g dissolved in 4 drops of water) and methanol (10 mL) was heated at 60° C. under a nitrogen atmosphere for 12 hr. The resulting material was washed with MeOH (3×500 mL), and then washed with 2M NaCL (3×500 mL), and then with water (2.0 L). The polymer was then suspended in water (1 L) and this suspension was acidified with conc HCl to pH 2.7. After filtration, the polymer was dried at 60° C. in a forced-air oven to give 6.0 g of a solid.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A method for lowering the serum phosphate level of a patient comprising administering to the patient a therapeutically effective amount of a polymer characterized by a substituted or unsubstituted diallylamine repeat unit.

2. The method of claim 1 wherein the polymer is a homopolymer.

3. The method of claim 1 wherein the polymer is a copolymer.

4. The method of claim 1 wherein the polymer is characterized by a repeat unit of the general formula

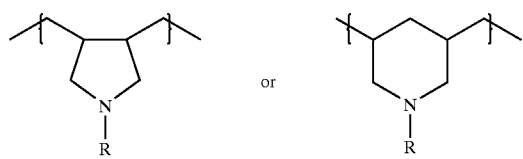

wherein R is a hydrogen atom, a substituted or unsubstituted normal, branched or cyclic alkyl group or a substituted or unsubstituted aryl group.

5. The method of claim 4 wherein R is an alkyl or aryl substituted with one or more substituents selected from the group consisting of fluorine, chlorine, bromine, iodine, alkyl, hydroxy, primary, secondary and tertiary amino, quaternary ammonium, alkoxy, carboxamido, sulfonamido, aryl, hydrazido, guanadyl, and ureyl.

6. The method of claim 4 wherein R is a $C_1$–$C_{12}$-alkyl group.

7. The method of claim 6 wherein R is an n-decyl group.

8. The method of claim 6 wherein R is a methyl group.

9. The method of claim 1 wherein the polymer comprises a repeat unit of the general formula

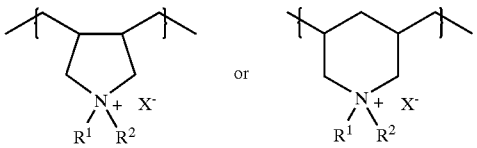

wherein $R^1$ and $R^2$ are each, independently, is hydrogen, a substituted or unsubstituted, normal, branched or cyclic alkyl group, or a substituted or unsubstituted aryl group; or $R^1$, $R^2$ and the nitrogen atom together form a cyclic system; and $X^-$ is a pharmaceutically acceptable anion.

10. The method of claim 9 wherein $X^-$ is a conjugate base of an acid selected from the group consisting of hydrochloric acid, hydrobromic acid, citric acid, tartaric acid, lactic acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

11. The method of claim 9 wherein $R^1$ is a normal or branched $C_1$–$C_{12}$-alkyl group.

12. The method of claim 11 wherein $R^1$ is methyl.

13. The method of claim 12 wherein $R^2$ is hydrogen.

14. The method of claim 11 wherein $R^1$ is decyl.

15. The method of claim 14 wherein $R^2$ is hydrogen.

16. The method of claim 9 wherein $R^1$ is an alkyl or aryl group substituted with one or more substituents selected from the group consisting of fluorine, chlorine, bromine, iodine, alkyl, hydroxy, primary, secondary and tertiary amino, quaternary ammonium, alkoxy, carboxamido, sulfonamido, aryl, hydrazido, guanadyl, and ureyl.

17. The method of claim 9 wherein $R^1$ and $R^2$ together form a substituted or unsubstituted $C_2$–$C_{12}$-alkylene group.

18. The method of claim 17 wherein $R^1$ and $R^2$ together form —$(CH_2)_n$—, wherein n is an integer from 2 to about 12.

19. The method of claim 1 wherein the polymer is cross-linked.

20. The method of claim 19 wherein the polymer is crosslinked by a multifunctional co-monomer.

21. The method of claim 20 wherein the multifunctional co-monomer is selected from the group consisting of diacrylates, triacrylates, tetraacrylates, dimethacrylates, diacrylamides, dimethacrylamides, diallylacrylamides and polyvinylarenes.

22. The method of claim 21 wherein the multifunctional comonomer is selected from the group consisting of ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), bisphenol A dimethacrylate, bisphenol A diacrylate, pentaerythritol tetraacrylate, trimethylolpropane triacrylate and divinylbenzene.

23. The method of claim 20 wherein the multifunctional comonomer is a multifunctional diallylamine.

24. The method of claim 23 wherein the multifunctional diallylamine is a bis(diallylamino)alkane or a bis(diallylalkylammonio)alkane.

25. The method of claim 24 wherein the multifunctional diallylamine is 1,10-bis(diallylmethylammonio)decane dibromide.

26. The method of claim 19 wherein the polymer is crosslinked by a bridging unit selected from the group consisting of straight chain or branched, substituted or unsubstituted alkylene groups, diacylalkylene groups, diacylarene groups and alkylene bis(carbamoyl) groups.

27. The method of claim 26 wherein the bridging units are selected from the group consisting of —$(CH_2)_n$—,
wherein n is an integer from about 2 to about 20;
—$CH_2$—$CH(OH)$—$CH_2$—; —$C(O)CH_2CH_2C(O)$—;
—$CH_2$—$CH(OH)$—$O$—$(CH_2)_m$—$O$—$CH(OH)$—$CH_2$—, wherein m is 2 to about 4; —$C(O)$—$(C_6H_2(COOH)_2)$—$C(O)$—; and
—$C(O)NH(CH_2)_pNHC(O)$—, wherein p is an integer from about 2 to about 20.

28. A method of lowering the serum phosphate level of patient comprising administering to the patient a therapeutically effective amount of polymer comprising a first monomer of the general formula

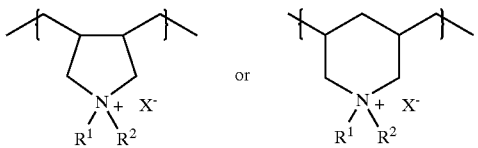

wherein $R^1$ and $R^2$ are each, independently, a substituted or unsubstituted normal, branched or cyclic alkyl group or a substituted or unsubstituted aryl group; or $R^1$, $R^2$ and the nitrogen atom together form a cyclic system; and $X^-$ is a pharmaceutically acceptable anion; and a second monomer of the general formula

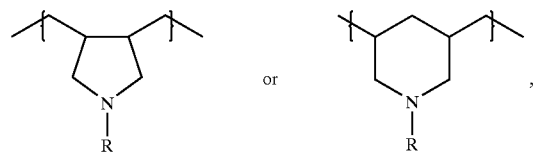

wherein R is a hydrogen atom, a substituted or unsubstituted normal, branched or cyclic alkyl group or a substituted or unsubstituted aryl group.

* * * * *